United States Patent
Hrakovsky et al.

(12)

(10) Patent No.: US 7,749,536 B2
(45) Date of Patent: Jul. 6, 2010

(54) PHARMACEUTICAL FORMULATIONS OF ALIPHATIC AMINE POLYMERS AND METHODS FOR THEIR MANUFACTURE

(75) Inventors: Julia Hrakovsky, Rosh Ha-Ayin (IL); Ruth Tenengauzer, Raanana (IL); Alla Ioffe, Kfar-Saba (IL); Eleonora Moin-Kotliar, Herzlia (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 72 days.

(21) Appl. No.: 11/354,555

(22) Filed: Feb. 14, 2006

(65) Prior Publication Data

US 2007/0190020 A1 Aug. 16, 2007

(51) Int. Cl.
*A61K 9/20* (2006.01)
(52) U.S. Cl. .................. 424/465; 424/78.08; 424/78.1; 424/464
(58) Field of Classification Search ........................ None
See application file for complete search history.

(56) References Cited

U.S. PATENT DOCUMENTS

| | | | | |
|---|---|---|---|---|
| 4,928,840 | A | * | 5/1990 | Barshay et al. ............... 220/8 |
| 6,733,780 | B1 | | 5/2004 | Tyler et al. |
| 2002/0035089 | A1 | | 3/2002 | Barbier et al. |
| 2005/0131138 | A1 | * | 6/2005 | Connor et al. ............... 524/612 |
| 2005/0260236 | A1 | | 11/2005 | Tyler et al. |

FOREIGN PATENT DOCUMENTS

| | | |
|---|---|---|
| EP | 0 997 148 A1 | 5/2000 |
| EP | 1 153 940 A1 | 11/2001 |
| WO | WO01/21211 * | 3/2001 |

OTHER PUBLICATIONS

DOW Excipients disclosure, downloaded from the world wide web on May 27, 2008.*
Engineering Systems disclosure "Some Information on Tablet Hardness Testing" downloaded from the world wide web on May 7, 2008.*
FDA Renagel disclosure Jul. 14, 2000.*
European Search Report, issued Aug. 29, 2006, for European Patent Application No. 06250788.4, filed Feb. 14, 2006.

* cited by examiner

*Primary Examiner*—Eric E. Silverman
(74) *Attorney, Agent, or Firm*—Kenyon & Kenyon LLP

(57) ABSTRACT

The present invention provides pharmaceutical compositions comprising aliphatic amine polymers such as for example Sevelamer HCl as the active pharmaceutical ingredient, wherein the aliphatica amine polymers are spray granulated. The present invention further provides methods of preparing stable pharmaceutical compositions of aliphatic amine polymers such as for example Sevelamer HCl, preferably in tablets dosage forms.

26 Claims, No Drawings

PHARMACEUTICAL FORMULATIONS OF ALIPHATIC AMINE POLYMERS AND METHODS FOR THEIR MANUFACTURE

FIELD OF THE INVENTION

The present invention relates to pharmaceutical compositions comprising aliphatic amine polymers, such as for example Sevelamer HCl, as the active pharmaceutical ingredient and methods of preparing pharmaceutical compositions thereof, such as for example Sevelamer HCl Film Coated Tablets employing wet granulation.

BACKGROUND OF THE INVENTION

Aliphatic amine polymers are useful as active pharmaceutical ingredients for use in pharmaceutical compositions. A particularly interesting aliphatic amine polymer is Sevelamer, a polymeric phosphate binder intended for oral administration. Sevelamer hydrochloride is a poly(allylamine hydrochloride) crosslinked with epichlorohydrin in which forty percent of the amines are apparently protonated. It is known chemically as poly(allylamine-co-N,N'-diallyl-1,3-diamino-2-hydroxypropane) hydrochloride. Sevelamer hydrochloride is hydrophilic, but insoluble in water. The reported structure of Sevelamer HCl is represented below:

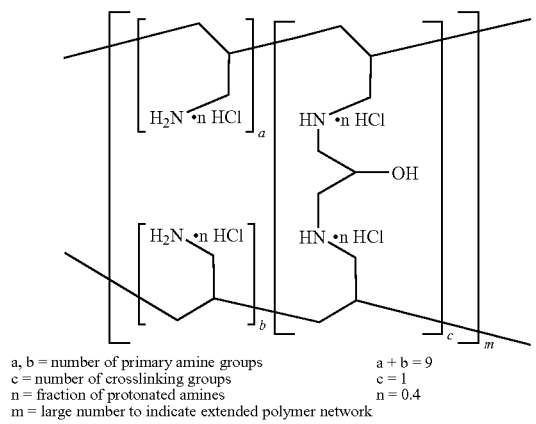

a, b = number of primary amine groups     a + b = 9
c = number of crosslinking groups     c = 1
n = fraction of protonated amines     n = 0.4
m = large number to indicate extended polymer network Sevelamer HCl is currently being marketed as RENAGEL®, for the treatment of patients with Chronic Kidney Disease (CKD) which are on hemodialysis[1]. According to the prescribing information RENAGEL® is indicated for the control of serum phosphorus in such CKD patients. In general, commercially available Sevelamer tablets also contain the following inactive ingredients; hypromellose, diacetylated monoglyceride, colloidal silicon dioxide, and stearic acid.

[1] Renagel® is sold by Genzyme Corporation. The Prescribing Information is available from www.renagel.com/docs/renagel_pi.pdf which describes the 400 mg and 800 mg tablets as containing the following inactive ingredients: hypromellose, diacetylated monoglyceride, collodial silicon dioxide and stearic acid.

The method of producing a direct compressible composition of a polymer tablet core is described in U.S. Pat. No. 6,733,780 B1 and U.S. Patent Application 2005/0260236 A1. These references describe Sevelamer HCl as a product which compressibility is strongly dependent upon the degree of hydration. Apparently, hydrating the polymer to the desired moisture level is considered by those inventors as an essential first step in manufacturing the finished product.

Further, Sevelamer HCl is known to be very hygroscopic and swell upon contact with water. Such swelling of the aliphatic amine polymer Sevelamer complicates formulating the active pharmaceutical ingredient in a pharmaceutical composition. Thus although compressibility is apparently dependant on the degree of hydration, simply adding water to sevelamer results in a swollen material which swollen material is impossible to use to press tablets. The present invention overcomes this problem of swelling of the active pharmaceutical ingredient by providing a more compressible sevelamer formulation within which the water content of sevelamer is not significantly increased compared to the commercially available sevelamer raw material. Even when using a wet granulation method with the present sevelamer formulation, the active pharmaceutical ingredient sevelamer has not swollen significantly. It is noted that commercially available sevelamer raw material is similarly impossible to compress.

SUMMARY OF THE INVENTION

In one aspect the present invention provides a pharmaceutical composition comprising, a) aliphatic amine polymers, and b) at least one pharmaceutical excipient, wherein the aliphatic amine polymer in the composition comprises wet granulated aliphatic amine polymers. Preferably, the aliphatic amine polymer is Sevelamer HCl or another pharmaceutically acceptable salt of Sevelamer, such as for example Sevelamer Carbonate. The granulation liquid for preparing the wet granulation of aliphatic amine polymers is preferably a combination of an organic solvent and water or where the solvent is ethanol, no water may be required.

Further, there is provided a method of preparing a granular composition comprising wet granulated aliphatic amine polymers comprising the following steps of a) providing aliphatic amine polymers;

b) providing at least one organic solvent preferably together with water to form a granulating solution, which can optionally contain one or more excipients such as a binder;

c) contacting the granulating solution with the aliphatic amine polymers by preferably spraying it onto the aliphatic amine polymers and one or more excipients and forming a wet granulate, more preferably performed in a fluidized bed drier; and d) mixing the wet granulate with one or more excipients and forming a final blend.

Preferred wet granulation solutions are ethanolic or preferably ethanol/water solutions.

Furthermore, the method preferably further comprises the steps of e) pressing the final blend into tablets.

Alternatively, the method further comprises the step of e) filling capsules with the final blend.

In another aspect, the present invention provides a pharmaceutical composition comprising wet granulated aliphatic amine polymers, preferably manufactured by spray granulation techniques, wherein the pharmaceutical composition has a degree of hydration of less than about 7% as measured by Karl Fischer (KF) analysis and is compressible and suitable for tableting.

In another aspect, the present invention provides a method of treating a patient suffering from chronic kidney disease comprising administering in combination with hemodialysis a therapeutically effective amount of Sevelamer HCl in a pharmaceutical composition comprising wet granulated Sevelamer HCl.

DETAILED DESCRIPTION OF THE INVENTION

To achieve an adequate protection against swelling upon contact with water of highly hygroscopic active pharmaceutical ingredients such as aliphatic amine polymers in a pharmaceutical composition is an important aspect in formulating a dosage form of aliphatic amine polymers for use in medical treatments. A preferred aliphatic amine polymer composition for use in the formulations of the present invention is Sevelamer HCl. According to the present invention, formulations of aliphatic amine polymers with a low hydration level and which are highly compressible can be achieved when the aliphatic amine polymers are wet granulated with a granulating solution comprising organic solvents preferably mixed with water optionally containing one or more of a binder. In addition, these formulations of aliphatic amine polymers of the present invention have a lower hydration level compared to that of the Renagel® formulations. Moreover, the aliphatic amine polymers in the pharmaceutical composition of the present invention have a similarly low hydration level when compared to the aliphatic amine polymer raw material prior to its use in such pharmaceutical composition. The wet granulation is preferably achieved by techniques of spray granulation. These pharmaceutical compositions according to the present invention are easily prepared and have good storage properties. The present invention thus provides a pharmaceutical composition comprising aliphatic amine polymers wherein the objective of providing a compressible wet granulated formulation of for example sevelamer with a desired protection against the swelling propensity of the active ingredient in such pharmaceutical compositions. This objective is achieved by using a formulation wherein the aliphatic amine polymers are wet granulated with at least one organic solvent preferably mixed with water, most preferably by spray wet granulation.

In a first approach developing a pharmaceutical composition comprising aliphatic amine polymers, tablets were produced using a conventional direct compression method. However, the material of the aliphatic amine polymer formulation was determined to be not compressible. Secondly, a wet granulation method was attempted using a high shear mixer employing water as the only granulating liquid. Similarly, the method was determined to be not suitable because of swelling of the active material during the granulation process due to the use of water as the only granulating liquid. As a consequence, the material for the aliphatic amine polymer formulation is not compressible. In contrast, it was surprisingly found that using an ethanol/water granulation solution, as for example in a wet granulation method with such ethanol/water solution, is an appropriate method for producing Sevelamer tablets. The spray granulation technique is particularly favored.

One embodiment of the present invention provides a pharmaceutical composition comprising, a) granulated aliphatic amine polymers, and b) at least one pharmaceutical excipient, wherein the aliphatic amine polymer in the composition comprises preferably wet granulated, more preferably spray wet granulated aliphatic amine polymers. Moreover, granulated aliphatic amine polymers are preferably granulated employing a granulating liquid of an organic solvent/water mixture. Suitable granulation liquids are ethanol, ethanol/water, isopropyl/water, and mixtures thereof. Preferably, the granulation liquid comprises about 82% to about 95% ethanol (95%) and about 5% to about 18% water. More preferably, the granulation liquid comprises 95% ethanol and 5% water. Furthermore, the aliphatic amine polymer is preferably Sevelamer HCl or another pharmaceutical acceptable salt of Sevelamer such as for example Sevelamer Carbonate, more preferably the aliphatic amine polymer is Sevelamer HCl. Moreover, the pharmaceutical composition comprises preferably from about 60% to about 95% by weight of Sevelamer HCl, more preferably from about 65% to about 85%, most preferably from about 65% to about 80% by weight of Sevelamer HCl. Furthermore, the Sevelamer HCl in the pharmaceutical composition is preferably substantially non-hydrated Sevelamer HCl.

In another embodiment, the present invention provides a pharmaceutical composition comprising spray granulated aliphatic amine polymers, wherein the pharmaceutical composition has a degree of hydration of less than about 7% as measured by Karl Fischer analysis. Preferably, the aliphatic amine polymer is Sevelamer HCl or another pharmaceutically acceptable salt of Sevelamer, such as for example Sevelamer Carbonate. More preferably the aliphatic amine polymer used in the process for manufacturing the formulation is a substantially non-hydrated aliphatic amine polymer. Furthermore, in the form of a tablet such pharmaceutical composition preferably has a hardness of at least about 17 Strong Cobb Units (SCU), more preferably from about 17 SCU to about 40 SCU. Further, such tableted pharmaceutical composition of the present invention preferably has a friability of less than about 1%, more preferably less than 0.1%. Moreover, such tableted pharmaceutical composition of the present invention preferably has a disintegration time in 0.1N HCl of less than about 5 minutes, more preferably from about 2 ½% to about 3 minutes.

Suitable granulation solutions/liquids for use in the present invention include ethanolic solutions (ethanol), ethanol/water, or isopropyl alcohol/water solutions. More preferably, the granulation solution is an ethanol/water solution. Preferably, the granulation liquid comprises about 82% to about 95% ethanol (95%) and about 5% to about 18% water. More preferably, the granulation liquid comprises 95% ethanol and 5% water.

The pharmaceutical compositions of wet granulated, preferably wet spray granulated, aliphatic amine polymers of the present invention may further contain excipients such as tablet and capsule fillers and diluents (such as microcrystalline cellulose, lactose, starch and tri-basic calcium phosphate), disintegrants (such as starch, croscarmellose sodium, crospovidone and sodium starch glycolate), binders (such as starch, hydroxypropyl methyl cellulose and Povidone), glidant (such as colloidal silicon dioxide), lubricants (such as magnesium stearate, magnesium lauryl sulfate, stearic acid and sodium stearyl fumarate).

More particularly, suitable diluents and fillers for use in the pharmaceutical composition of the present invention include microcrystalline cellulose (e.g. Avicel®), lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydroxyethyl cellulose, hydroxypropyl cellulose (e.g. Klucel®), hydroxypropyl methyl cellulose (e.g. Methocel®), liquid glucose, maltodextrin, methylcellulose, polymethacrylates, povidone (e.g. Povidone PVP K-30, Kollidon®, Plasdone®), pregelatinized starch, sodium alginate and starch. Furthermore, Povidone has been found to be a particularly useful binder. Moreover, this binder is preferably added as a solution in the granulating liquid.

A compacted solid pharmaceutical composition may also include the addition of a disintegrant to the composition. Disintegrants include croscarmellose sodium (e.g. Ac Di Sole, Primellose®), crospovidone (e.g. Kollidon®, Polyplasdone®), microcrystalline cellulose, polacrilin potassium, powdered cellulose, pregelatinized starch, sodium starch glycolate (e.g. Explotab®, Primoljel®) and starch.

Glidants can be added to improve the flowability of a solid composition before compaction and to improve the accuracy of dosing especially during compaction and capsule filling. Excipients that may function as glidants include colloidal silicon dioxide, magnesium trisilicate, powdered cellulose, and talc.

A lubricant can be added to the composition to reduce adhesion and/or ease the release of the product from e.g. the dye. Lubricants include magnesium stearate, calcium stearate, glyceryl monostearate, glyceryl palmitostearate, hydrogenated castor oil, hydrogenated vegetable oil, mineral oil, polyethylene glycol, sodium lauryl sulfate, sodium stearyl fumarate, stearic acid, talc and zinc stearate.

Other excipients that may be incorporated into the formulation include preservatives, surfactants, antioxidants, or any other excipient commonly used in the pharmaceutical industry.

The solid compositions of the present invention include powders, granulates, aggregates and compacted compositions. The dosages include dosages suitable for oral, buccal, and rectal administration. Although the most suitable administration in any given case will depend on the nature and severity of the condition being treated, the most preferred route of the present invention is oral. The dosages may be conveniently presented in unit dosage form and prepared by any of the methods well known in the pharmaceutical arts.

The pharmaceutical composition of the present invention may be prepared in any dosage form such as a compressed granulate in the form of a tablet for example. Also, uncompressed granulates and powder mixes that are obtained by the method of the present invention in the pre-compression steps can be simply provided in dosage form of a capsule or sachet. Therefore, dosage forms of pharmaceutical composition of the present invention include solid dosage forms like tablets, powders, capsules, sachets, troches and losenges. The dosage form of the present invention may also be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

Once an alphatic amine polymer, preferably Sevelamer HCl, solid composition is prepared in accordance with the present invention, it is preferably formulated into pharmaceutical formulations such as conventional dosage forms, including tablets and capsules. Tablets are preferred dosage forms. In addition, the tablets may be coated with an optional cosmetic tablet coating.

The present invention also provides a method of preparing pharmaceutical compositions comprising aliphatic amine polymers such as for example Sevelamer HCl. Preferably, the method of the present invention produces compressed solid dosage forms. There are three well known processes for manufacturing such dosage forms; (i) direct compression, (ii) dry granulation and (iii) wet granulation. There are two well known processes for wet granulation. A wet granulate can be prepared using a mixer and subsequently the wet granulate is dried in order to obtain a dry homogenous granulate. In another method a wet granulate is prepared by spray granulation. In a fluid-bed, spray granulation process, particles and granulate are built up in a fluid bed by spraying a liquid onto fluidized particles. Thus in such process materials are fluidized in the fluid bed dryer and subsequently a solution is sprayed through a nozzle. The choice of processing approach depends upon the properties of the drug and chosen excipients, for example particle size, blending compatibility, density and flowability. For preparing Sevelamer HCl tablets, granulation is preferred, wherein wet granulation being the most preferred with the technique of spray granulation being the method of choice. In addition, the tablets may also be coated to assure ease of swallowing or to provide an elegant appearance.

In one embodiment, the present invention provides a method of preparing a pharmaceutical composition comprising wet granulated aliphatic amine polymers comprising the steps of
 a) providing aliphatic amine polymers;
 b) wet granulating the aliphatic amine polymers with one or more excipients and forming a pharmaceutical composition. Preferred wet granulation solutions for use in this method of the present invention are ethanolic, ethanol/water, or isopropyl alcohol/water solutions. More preferably, the wet granulation solution is an ethanol/water solution, and most preferably a solution of about 82% to about 95% ethanol (95%) and about 5% to about 18% water. Most preferred is a wet granulation solution of 95% ethanol (95%) and 5% water.

In another embodiment, the present invention provides a method of preparing a granular composition comprising spray granulated aliphatic amine polymers comprising the following steps of
 a) providing aliphatic amine polymers;
 b) preparing a granulating liquid comprised of at least one organic solvent preferably mixed with water and optionally a binder preferably in the form of a solution;
 c) spraying the granulating liquid onto aliphatic amine polymers and one or more excipients and forming a spray granulate; and
 d) mixing the spray granulate with one or more excipients and forming a final blend.

Preferably the aliphatic amine polymer is Sevelamer HCl, more preferably the Sevelamer HCl used in the method is substantially non-hydrated Sevelamer HCl.

Preferably, the method further comprises the steps of
 e) pressing the final blend into tablets.

Alternatively, the method further comprises the steps of
 e) filling capsules with the final blend.

Specifically, the preferred method for the production of a pharmaceutical composition of wet granulated aliphatic amine polymers involves spraying of a granulating liquid or solution onto aliphatic amine polymers. The spraying process preferably uses Fluidized bed technology equipment, where the particles are suspended in a vertical column with a rising air stream. While the particles are fluidized, the granulating solution is sprayed into the column. This spraying can be carried out by any one of three methods; top spray, bottom spray and a "tangential" or powder spray. Preferably the spraying is carried out by a top spray method.

Spray granulation solutions suitable for use in a spray granulated process need to be selected according to requirements some of which are dependent on the physical properties of the active pharmaceutical ingredient. For example the granulation solutions should not alter the physical characteristics of and/or dissolve the active pharmaceutical ingredient.

Preferred spray granulation solutions for use in the method of the present invention are ethanolic, ethanol/water, or isopropyl alcohol/water solutions or mixtures thereof. More preferably, the spray granulation solution is an ethanol/water solution, and most preferably a solution of about 82% to about 95% ethanol (95%) and about 5% to about 18% water. Most preferred is a spray granulation solution of 95% ethanol (95%) and 5% water.

The Sevelamer pharmaceutical compositions in the form of film coated tablets prepared by the described method may contain per tablet various amounts of Sevelamer HCl and preferably contain either about 400 mg or about 800 mg of Sevelamer HCl as calculated on an anhydrous basis.

In another embodiment, the present invention provides a method of treating a patient suffering from chronic kidney disease comprising administering in combination with hemodialysis a therapeutically effective amount of Sevelamer HCl in a pharmaceutical composition comprising spray granulated Sevelamer HCl. Patients suffering from chronic kidney disease CKD are frequently treated with hemodialysis. In such patients, which are treated with hemodialysis, it is important to control the phosphorus content in their serum. Sevelamer HCl binds phosphorus and is therefore used as a phosphorus scavenger in the blood stream of patients to control serum phosphorus content. Thus the present invention provides a method of treating a patient suffering from chronic kidney disease and undergoing hemodialysis treatment comprising administering a therapeutically effective amount of Sevelamer HCl in a pharmaceutical composition comprising wet granulated, preferably wet spray granulated, Sevelamer HCl. Preferably, the method of treating a patient undergoing hemodialysis comprising administering a therapeutically effective amount of Sevelamer HCl in a pharmaceutical composition comprising wet granulated Sevelamer HCl controls the serum phosphorus content in such patient.

The scope of the invention should not be limited to the working examples, which are for demonstration purposes. One skilled in the art can practice the invention based on the disclosures in the present patent application.

EXAMPLES

Renagel® Tablets and Sevelamer HCl Active Ingredient

The tablets of the following examples 1 and 2 (tablets A and B respectively) were prepared according to the formulations and methods of the invention. Certain physical properties of these tablets A and B were determined as shown in Table 1 of example 3. Some of these physical properties were also determined for a comparative RENAGEL® tablet as presented in Table 3. In addition to the physical properties of tablets A and B some physical properties of the Sevelamer HCl active ingredient as used in the preparations of Examples 1 and 2 were determined. The active ingredient Sevelamer HCl used in the following examples was manufactured by Shasun Chemicals and Drugs Ltd with the following properties as shown in Table 1.

TABLE 1

Properties of Sevelamer raw material.

| Lot No. | Karl Fischer | Loss on drying (LOD) |
|---|---|---|
| RLB 054M0327 | 4.6% | 11.4% |

It is understood that, while the LOD result is indicative of all the material that can be evaporated or removed by heat or drying, it is the Karl Fischer analysis that determines the water content or level of hydration of the material tested.

Example 1

Tablet A of 400 mg Spray Granulated Sevelamer HCl

| Ingredient | K-35987*<br>mg/tablet |
|---|---|
| Part 1 | |
| Sevelamer HCl | 400.0 |
| Povidone | 28.0 |
| Ethanol/Water granulating liquid | |
| Part 2 | |
| Low-Substituted Hydroxypropyl Cellulose | 177.0 |
| Hydrogenated Vegetable Oil | 10.0 |
| Part 3 | |
| +Opadry ® | 9.45 |

*Batch number
+commercially available mix of polymer, plasticizer and opacifying agent The Sevelamer HCl was spray-granulated using a Povidone solution in mixture of ethanol/water as a granulating liquid. The granulate was blended with Part II ingredients. The final blend was compressed into tablet core and coated using Part III material. The solvents in the granulating liquid were comprised of either a mixture of 95% Ethanol (95%) and 5% water or a mixture of 82% Ethanol (95%) and 18% water.

Example 2

Tablet B of 800 mg Spray Granulated Sevelamer HCl

| Ingredient | K-36180*<br>mg/tablet |
|---|---|
| Part 1 | |
| Sevelamer HCl | 800.0 |
| Povidone | 56.0 |
| Ethanol/Water granulating liquid | |
| Part 2 | |
| Low-Substituted Hydroxypropyl Cellulose | 299.5 |
| Hydrogenated Vegetable Oil | 16.0 |
| Part 3 | |
| +Opadry ® | 39.0 |

*Batch number
+commercially available mix of polymer, plasticizer and opacifying agent The Sevelamer HCl was spray-granulated using a Povidone solution in mixture of ethanol/water as a granulating liquid. The obtained granulate was blended with Part II ingredients. The final blend was compressed into tablet core and coated using Part III material. The solvents in the granulating liquid were comprised of either a mixture of 95% Ethanol (95%) and 5% water or a mixture of 82% Ethanol (95%) and 18% water.

Example 3

Properties of Sevelamer HCl Preparation of Working Examples

The Sevelamer HCl tablets prepared according to the present invention were subjected to various analyses to determine their physical properties. The following Table 2 shows the results thereof and lists the obtained values for the physical properties of the tablets according to examples 1 and 2.

TABLE 2

Physical properties of Sevelamer HCl preparations.

| Example (Batch No.) | Flowability | LOD of the granulate | Hardness | Friability | KF | Disintegration time (HCl) (min) |
|---|---|---|---|---|---|---|
| 1 (K-35987) | Very Good | 10.3 | 17 SCU | 0.1% | 5.38 - cores | 2:34 |
| 2 (K-36180) | Very Good | 12.2 | 40 SCU | 0% | 5.35 - cores<br>6.5 - coated tablets | 2:36 |

The obtained granulates have very good or excellent flowability. Further, no swelling of the active material was observed to have occurred during the granulation process. Moreover, the compressed tablets have acceptable physical characteristics and disintegration times. The results obtained by Karl Fischer analysis indicate that tablets are produced without a significant change in the water content or Hydration level as evidenced by the KF value. The preferred hydration value as measured by Karl Fischer analysis can therefore be set at not more than 7%. In the following Table 3 some of the physical properties for the commercially available Renagel® tablets are shown.

TABLE 3

Physical properties of Renagel Tablets.

| Lot no. | KF | LOD |
|---|---|---|
| #643105 | 10.4% | 9.4% |
| #35276A | 9.0% | 8.5% |

It can be seen that the material that can be removed by evaporation from the Renagel® tablets consists almost entirely of water. Evidence hereof is the close similarity between the results obtained from the LOD and KF analyses. In contrast, it can be observed that in the tablets of the present invention the water content or hydration level of the sevelamer in the preparations, as evidenced by the Karl Fischer analysis, is very similar to the levels found in the raw active material received from the supplier.

The invention claimed is:

1. A pharmaceutical composition in the form of a tablet dosage form comprising;
    a) wet granulated pharmaceutically acceptable salt of Sevelamer; and
    b) at least one pharmaceutical excipient, wherein the wet granulated pharmaceutically acceptable salt of Sevelamer are granulated using a granulation liquid of an organic solvent or organic solvent/water mixture; and the tablet has a hardness of at least 17 SCU wherein the granulation liquid is an ethanol/water solution of about 82% to about 95% of 95% ethanol and about 5% to about 18% water.

2. The pharmaceutical composition according to claim 1, wherein the ethanol/water solution is a solution of 95% of 95% ethanol and 5% water.

3. The composition according to claim 1, wherein the wet granulated pharmaceutically acceptable salt of Sevelamer are spray granulated.

4. The pharmaceutical composition according to claim 1, wherein the pharmaceutically acceptable salt of Sevelamer is selected from the group consisting of Sevelamer HCl and Sevelamer Carbonate.

5. The pharmaceutical composition according to claim 1, wherein the pharmaceutically acceptable salt of Sevelamer is Sevelamer HCl.

6. The pharmaceutical composition according to claim 5, wherein the amount of Sevelamer HCl calculated as anhydrous Sevelamer HCl is from about 400 mg to about 800 mg in each tablet.

7. The pharmaceutical composition according to claim 1, wherein Sevelamer HCl is substantially non-hydrated and which hydration level is similar in comparison to the hydration level of raw material Sevelamer HCl.

8. The pharmaceutical composition according to claim 1, wherein the amount of Sevelamer HCl is from about 60% to about 95% of the weight of the composition.

9. The pharmaceutical composition according to claim 1, wherein the tablet has a water content of less than 7% as measured by Karl Fischer analysis.

10. The pharmaceutical composition according to claim 1, wherein the tablet has a friability of less than about 1.0%.

11. The pharmaceutical composition according to claim 1, wherein the tablet has a disintegration time in 0.1N HCl of less than about 5 minutes.

12. A method of preparing a tablet composition comprising wet granulated aliphatic amine polymers comprising the following steps of
    a) providing pharmaceutically acceptable salt of Sevelamer;
    b) preparing a granulating solution or liquid wherein the granulating solution or liquid is an ethanol/water solution having from about 82% to about 95% of 95% ethanol and from about 5% to about 18% water;
    c) spraying the granulating liquid or solution onto pharmaceutically acceptable salt of Sevelamer forming a spray granulate; and
    d) mixing the spray granulate with one or more excipients forming a final blend; and
    e) pressing the final blend into a tablet 13. The method according to claim 12, wherein the granulating solution is an ethanol/water solution prepared from 95% of 95% ethanol and 5% water.

14. The method according to claim 12, wherein the granulating solution or liquid further comprises a binder material.

15. The method according to claim 14, wherein the binder material is dissolved in the granulating solution or liquid.

16. The method according to claim 15, wherein the binder material comprises povidone.

17. The method according to claim 12, wherein the one or more excipient comprises low-substituted Hydroxypropyl Cellulose, hydrogenated vegetable oil and combinations thereof.

18. The method according to claim 12, wherein spraying of the granulation liquid is carried out in a fluidized bed equipment.

19. The method according to claim 18, wherein spraying of the granulating liquid is carried out by using a spraying method selected from the group consisting of top spray, bottom spray, and tangential/powder spray.

20. The method according to claim 19, wherein the spraying method is the top spray method.

21. The method according to claim 12, further comprising the step of
f) coating the tablets.

22. The method according to claim 12, wherein the pharmaceutically acceptable salt of Sevelamer is selected from the group consisting of Sevelamer HCl and Sevelamer Carbonate.

23. The method according to claim 22, wherein the pharmaceutically acceptable salt of Sevelamer is Sevelamer HCl.

24. A method of treating a patient suffering from chronic kidney disease comprising administering a therapeutically effective amount of in a pharmaceutical composition of claim I in combination with hemodialysis treatment to a patient in need thereof.

25. The method of claim 24, wherein the pharmaceutically acceptable salt of Sevelamer is Sevelamer HCl.

26. The method according to claim 24, wherein the treatment with Sevelmer HCl controls serum phosphate in a patient suffering from chronic kidney disease which patient is on hemodialysis treatment.

* * * * *